US009015958B2

(12) United States Patent
Bloemendaal

(10) Patent No.: US 9,015,958 B2
(45) Date of Patent: Apr. 28, 2015

(54) METHOD AND SYSTEM TO SELECTIVELY DRY GRAIN IN A GRAIN BIN

(71) Applicant: CTB, Inc., Milford, IN (US)

(72) Inventor: Brent J. Bloemendaal, Zionsville, IN (US)

(73) Assignee: CTB, Inc., Milford, IN (US)

( * ) Notice: Subject to any disclaimer, the term of this patent is extended or adjusted under 35 U.S.C. 154(b) by 166 days.

(21) Appl. No.: 13/791,936

(22) Filed: Mar. 9, 2013

(65) Prior Publication Data

US 2014/0250717 A1    Sep. 11, 2014

(51) Int. Cl.
*F26B 9/06* (2006.01)
*F26B 3/06* (2006.01)
*F26B 9/08* (2006.01)
*F26B 21/08* (2006.01)
*F26B 25/00* (2006.01)
*F26B 25/22* (2006.01)

(52) U.S. Cl.
CPC . *F26B 9/063* (2013.01); *F26B 3/06* (2013.01); *F26B 9/08* (2013.01); *F26B 9/082* (2013.01); *F26B 21/08* (2013.01); *F26B 25/002* (2013.01); *F26B 25/22* (2013.01); *F26B 2200/06* (2013.01)

(58) Field of Classification Search
USPC .......... 34/381, 386, 435, 550, 166, 167, 170, 34/174, 175; 324/658, 664; 239/49.3; 700/28, 275, 277; 702/65
See application file for complete search history.

(56) References Cited

U.S. PATENT DOCUMENTS

| 2,655,734 | A |   | 10/1953 | Ohlheiser |
|-----------|---|---|---------|-----------|
| 2,935,009 | A | * | 5/1960  | Cloud et al. .................. 454/180 |
| 3,046,624 | A | * | 7/1962  | Dietert et al. ................... 34/612 |
| 3,966,124 | A |   | 6/1976  | Sukup |
| 4,043,051 | A | * | 8/1977  | Lussenden ........................ 34/77 |
| 4,356,641 | A | * | 11/1982 | Rosenau ........................ 34/537 |

(Continued)

FOREIGN PATENT DOCUMENTS

BR    PI0402135        9/2005
EP       2775239 A2 * 10/2014

(Continued)

OTHER PUBLICATIONS

Brock® Grain Spreader Brochure; Brock Grain Systems and Chore-Time Brock International; 2008.

(Continued)

*Primary Examiner* — Steve M Gravin
(74) *Attorney, Agent, or Firm* — Harness, Dickey

(57) ABSTRACT

A controller is coupled to a plurality of moisture sensors positioned within the grain bin at various spaced-apart locations. The controller determines a grain moisture level adjacent each moisture sensor and compares the grain moisture level to a predetermined maximum moisture level. The controller is coupled to a grain spreader that is configured to selectively distribute incoming grain into the grain bin and operates the spreader to distribute incoming grain to create a shortened airflow path through the grain that encompasses the moisture sensors having determined grain moisture levels above the predetermined maximum moisture level. The controller is coupled to a fan that is coupled to the grain bin and configured to provide airflow through the grain in the grain bin. The controller operates the fan to provide greater airflow through the grain along the shortened airflow path than is provided along airflow paths outside the shortened airflow path.

20 Claims, 8 Drawing Sheets

(56) References Cited

U.S. PATENT DOCUMENTS

| | | | |
|---|---|---|---|
| 4,916,830 A * | 4/1990 | Braun et al. | 34/550 |
| 5,020,701 A | 6/1991 | Donelson | |
| 5,403,141 A | 4/1995 | Rauser | |
| 5,603,359 A | 2/1997 | Geiser | |
| 5,651,193 A * | 7/1997 | Rhodes et al. | 34/531 |
| 5,735,319 A | 4/1998 | McNamara et al. | |
| 5,992,049 A * | 11/1999 | Trost | 34/528 |
| 6,088,929 A * | 7/2000 | Watson et al. | 34/167 |
| 6,098,305 A * | 8/2000 | Watson et al. | 34/167 |
| 6,923,389 B2 | 8/2005 | Shivvers | |
| 7,004,401 B2 * | 2/2006 | Kallestad | 236/49.3 |
| 7,931,432 B2 | 4/2011 | Hershberger | |
| 8,806,772 B1 * | 8/2014 | Schaefer, Jr. | 34/89 |
| 2003/0079365 A1 | 5/2003 | Corak et al. | |
| 2010/0229421 A1 * | 9/2010 | Salisbury | 34/524 |
| 2012/0003066 A1 | 1/2012 | Niemeyer et al. | |
| 2013/0014404 A1 * | 1/2013 | Bloemendaal | 34/167 |
| 2013/0015251 A1 * | 1/2013 | Bloemendaal et al. | 236/49.3 |
| 2014/0043048 A1 * | 2/2014 | Bloemendaal et al. | 324/664 |
| 2014/0046611 A1 * | 2/2014 | Bloemendaal et al. | 702/65 |
| 2014/0250717 A1 * | 9/2014 | Bloemendaal | 34/487 |

FOREIGN PATENT DOCUMENTS

| | | | | |
|---|---|---|---|---|
| JP | 200-111256 A | * | 2/1991 | |
| JP | 06281336 A | * | 10/1994 | F26B 23/00 |
| JP | H10-19462 A | | 1/1998 | |
| WO | WO 2013/020559 | | 2/2013 | |

OTHER PUBLICATIONS

Extended European Search Report dated Feb. 6, 2015 in corresponding European Patent Application No. 14158209.8.

OPI Systems: "Advanced Grain Management", Internet Citation, 2011, pp. 1-5, 22, XP002714203, Retrieved from the Internet: http://www.sirajsons.pk/OPI-Integris%20Presentation.pdf [retrieved on Oct. 4, 2013].

* cited by examiner

| Sensor Node Address | | | Raw Sensor Data | | | Sensor Node Location Data | | | Caclulated | | |
|---|---|---|---|---|---|---|---|---|---|---|---|
| Cable ID | Sensor Node ID | Temperature | Reference Capacitance | Moisture Capacitance | | X | Y | Z | Moisture Content | Grain Depth | Flag |
| 1 | 1 | | | | | | | | | | |
| 1 | 2 | | | | | | | | | | |
| 1 | 3 | | | | | | | | | | |
| 1 | 4 | | | | | | | | | | |
| 1 | . . . | | | | | | | | | | |
| 1 | x | | | | | | | | | | |
| 2 | 1 | | | | | | | | | | |
| 2 | 2 | | | | | | | | | | |
| 2 | 3 | | | | | | | | | | |
| 2 | 4 | | | | | | | | | | |
| 2 | . . . | | | | | | | | | | |
| 2 | x | | | | | | | | | | |
| . | 1 | | | | | | | | | | |
| . | 2 | | | | | | | | | | |
| . | 3 | | | | | | | | | | |
| x | 4 | | | | | | | | | | |
| x | . . . | | | | | | | | | | |
| x | x | | | | | | | | | | |

FIG. 13

METHOD AND SYSTEM TO SELECTIVELY DRY GRAIN IN A GRAIN BIN

FIELD

The present disclosure relates to drying grain in a grain bin.

BACKGROUND

This section provides background information related to the present disclosure which is not necessarily prior art.

Grain can be dried in grain storage bins by passing ambient or heated air through the grain. A controller can be coupled to a fan and heater to deliver an appropriate drying airflow to the grain bin. As the air passes through the grain, it has been understood that a horizontal drying front moves through the grain from the bottom of the grain bin toward the top. Thus, it has been considered important to provide a level grain surface within the grain bin to promote uniform airflow throughout the grain so the grain is uniformly dried and efficiency is promoted.

Such grain storage bins capable of drying grain can also include motorized grain spreaders to distribute incoming grain. As suggested above, the purpose of such spreaders is to provide a level grain surface to facilitate the uniform airflow. In addition, it is believed that such spreaders have a control system that is separate and distinct from any grain drying aeration system, including any fan and heater. In addition, it is believed such grain spreaders are operated, at all relevant times, in such a manner that maintains the level grain surface as much as possible.

Such grain storage bins capable of drying grain can additionally include grain removal augers. It is believed that such grain removal augers have a control system that is separate and distinct from any grain drying aeration system, including any fan and heater. In addition, it is believed that such grain removal augers have a control system that is separate and distinct from any grain spreader control system.

SUMMARY

This section provides a general summary of the disclosure, and is not a comprehensive disclosure of its full scope or all of its features; nor are the features summarized herein essential aspects of the disclosure.

In one aspect of the present disclosure a system for drying grain in a grain bin includes a plurality of moisture sensors positioned within the grain bin at various spaced-apart locations throughout the grain bin. The plurality of moisture sensors are coupled to a controller that is configured to determine a grain moisture level adjacent each moisture sensor. The controller is configured to compare each grain moisture level to a predetermined maximum moisture level. The controller is coupled to one of: a grain spreader configured to selectively distribute grain coming into the grain bin; a grain discharge auger configured to selectively remove grain from the grain bin; or both. The controller is configured to operate the one of: the grain spreader, the grain discharge auger, or both, to create a shortened airflow path encompassing the moisture sensors having determined grain moisture levels above the predetermined maximum moisture level. The controller is coupled to a fan associated with the grain bin and configured to provide airflow through grain in the grain bin. The controller is configured to operate the fan, wherein greater airflow is provided through the grain along the shortened airflow path than is provided along airflow paths through the grain outside the shortened airflow path.

In another aspect of the present disclosure a system for drying grain in a grain bin includes a plurality of capacitive moisture sensors positioned within the grain bin at various spaced-apart locations throughout the grain bin. The plurality of capacitive moisture sensors is coupled to a controller configured to determine a grain moisture level adjacent each capacitive moisture sensor. The controller is configured to compare each grain moisture level to a predetermined maximum moisture level. The controller is coupled to a variable speed grain spreader configured to selectively distribute grain coming into the grain bin. The controller is configured to operate the grain spreader to create one of an inverted cone-shaped grain surface, and a cone-shaped surface, wherein a shortened airflow path encompasses the moisture sensors having determined grain moisture levels above the predetermined maximum moisture level. The controller is coupled to a fan associated with the grain bin and configured to provide airflow through grain in the grain bin. The controller is configured to operate the fan, wherein greater airflow is provided through the grain along the shortened airflow path than is provided along airflow paths through the grain outside the shortened airflow path.

In yet another aspect of the present disclosure a method of drying grain in a grain bin includes coupling a controller to a plurality of moisture sensors positioned within the grain bin at various spaced-apart locations throughout the grain in the grain bin. The controller determines a grain moisture level adjacent each moisture sensor. The controller compares the grain moisture level to a predetermined maximum moisture level. The controller is coupled to a grain spreader configured to selectively distribute incoming grain into the grain bin. The controller operates the grain spreader to distribute incoming grain to create a shortened airflow path through the grain in the grain bin that encompasses the moisture sensors having determined grain moisture levels above the predetermined maximum moisture level. The controller is coupled to a fan that is coupled to the grain bin and configured to provide airflow through the grain in the grain bin. The controller operates the fan, wherein greater airflow is provided through the grain along the shortened airflow path than is provided along airflow paths through the grain outside the shortened airflow path.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 13 is a memory data structure map of the main controller of the system of FIG. 1.

Corresponding reference numerals indicate corresponding parts throughout the several views of the drawings.

DETAILED DESCRIPTION

Figure 1:
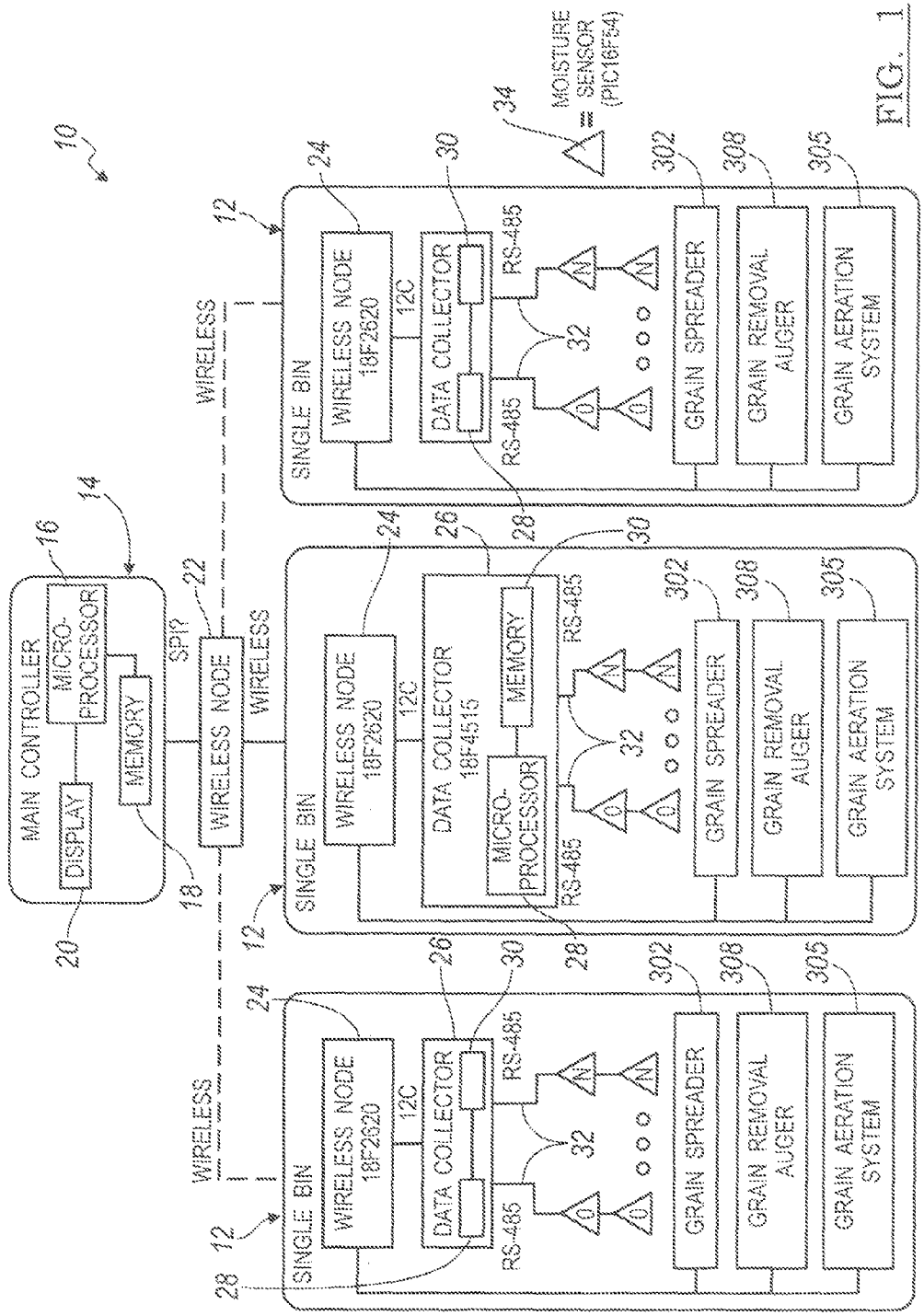
FIG. 1 is an overview of a system for drying grain in a grain bin in accordance with the present disclosure.

Example embodiments will now be described more fully with reference to the accompanying drawings. Numerous specific details are set forth in the exemplary embodiments described herein, such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Referring to FIG. 1, which provides a block diagram of a system 10 for drying grain in a plurality of grain bins 12. A farm or aggregator may include a plurality of grain bins 12 that are all controlled by a single main controller 14 including a microprocessor 16, memory 18, and a display 20. All of the memory described herein, including memory 18, is non-transitory computer-readable memory. Main controller 14 communicates with each grain bin 12 via wireless nodes 22, 24. For example wireless node 22 can be an 802.15 module and each wireless node 24 can include a PIC 18F2620 microprocessor.

A wireless node 24 of each grain bin 12 provides an input and output communication link between main controller 14 and various components of a grain bin 12, including a plurality of capacitive moisture sensors 34 positioned throughout grain bin 12 on one or more moisture cables 32, a grain spreader 302. Wireless node 24 of each grain bin 12 can also provide a communication link between main controller 14 and an aeration fan 304 and heater 306, and a grain removal auger 308. Thus, wireless node 24 for each grain bin 12 can be a single physical device, or can be separate physical devices, each being associated with one of: the capacitive moisture sensors 34, the grain spreader 302, the aeration fan 304, the heater 306, and the grain removal auger 308. Alternatively, any of the capacitive moisture sensors 34, the grain spreader 302, the aeration fan 304, the heater 306, and the grain removal auger 308 can be in communication with main controller 14 via a hard wired connection.

Each grain bin 12 has a data collector 26 including a microprocessor 28 and memory 30. For each grain bin 12, a plurality of moisture cables 32 are in communication with a data collector 26 including a microprocessor 28 and memory 30. Each moisture cable 32 includes a plurality of capacitive moisture sensor nodes 34 positioned at intervals along the length of each cable 32. Each sensor node 34 of each cable 32 is electrically coupled in parallel to data collector 26.

Figure 2:
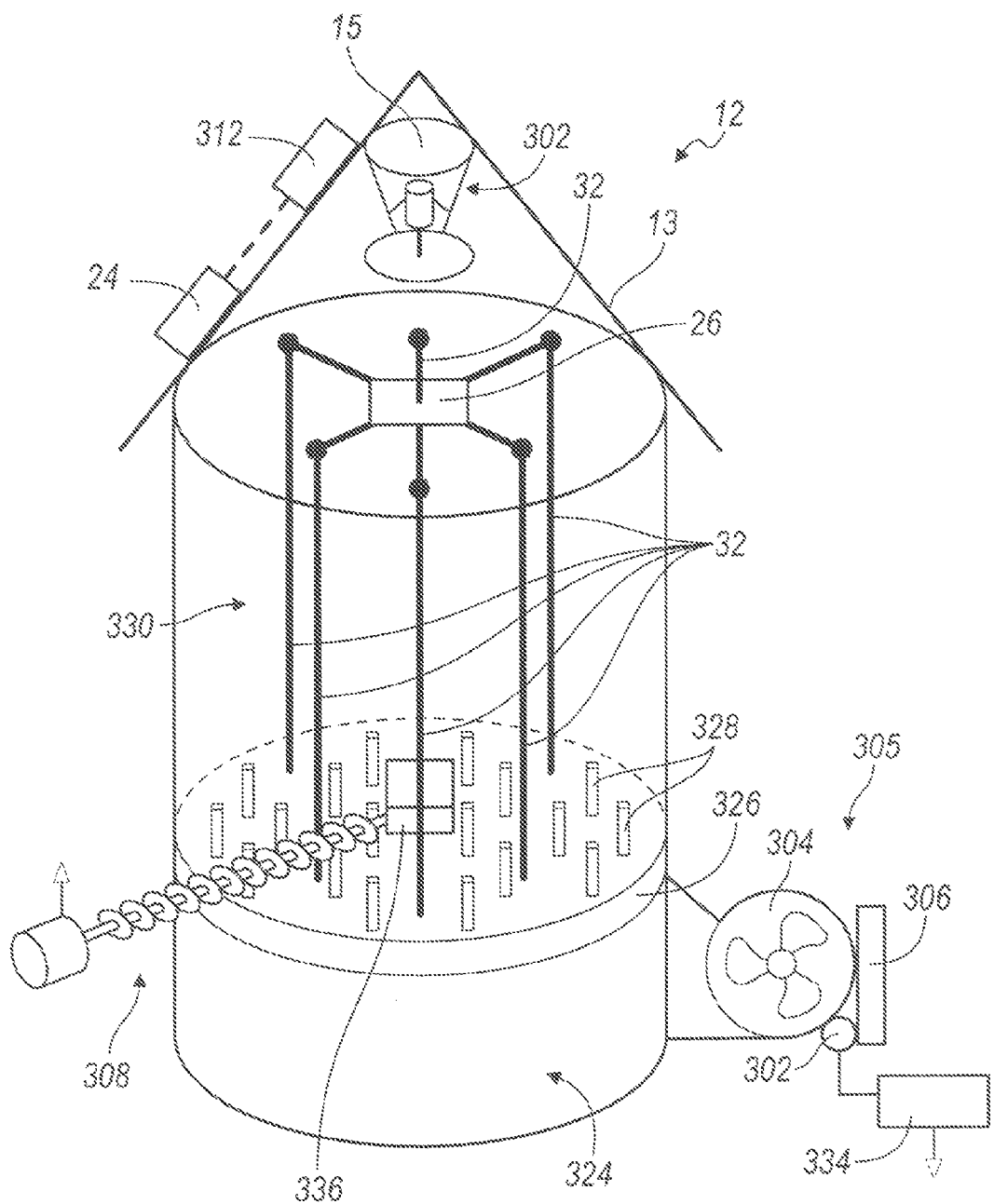
FIG. 2 is a perspective representation showing various components of the system of FIG. 1.
Figure 3:
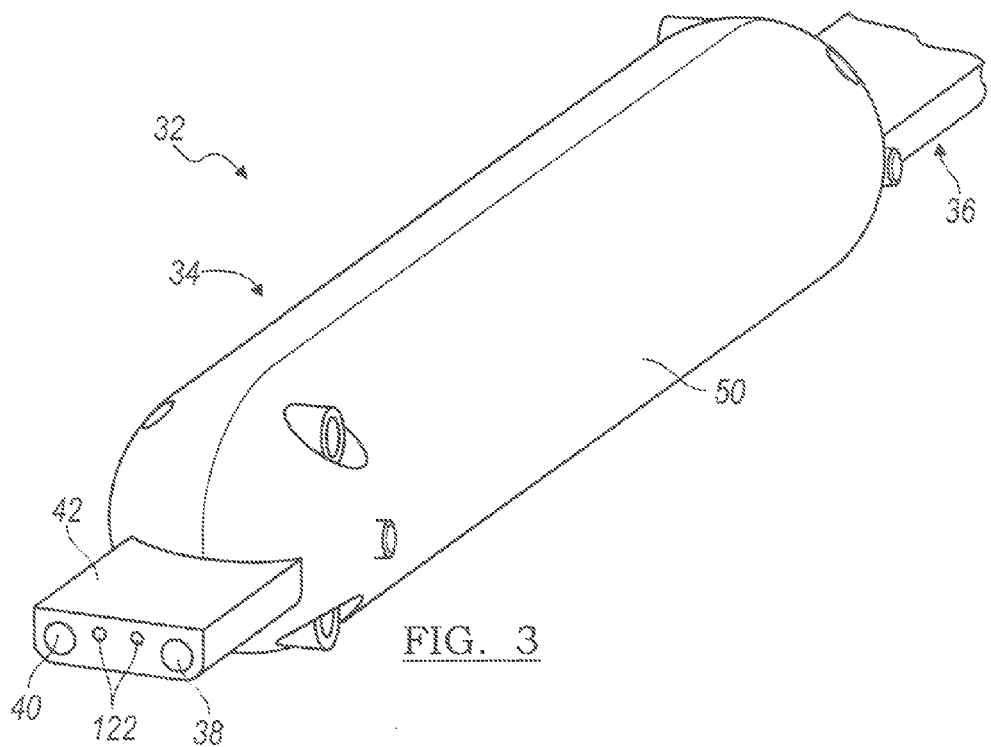
FIG. 3 is a perspective view of a capacitive moisture cable sensor node of a capacitive moisture cable of the system of FIG. 1.
Figure 4:
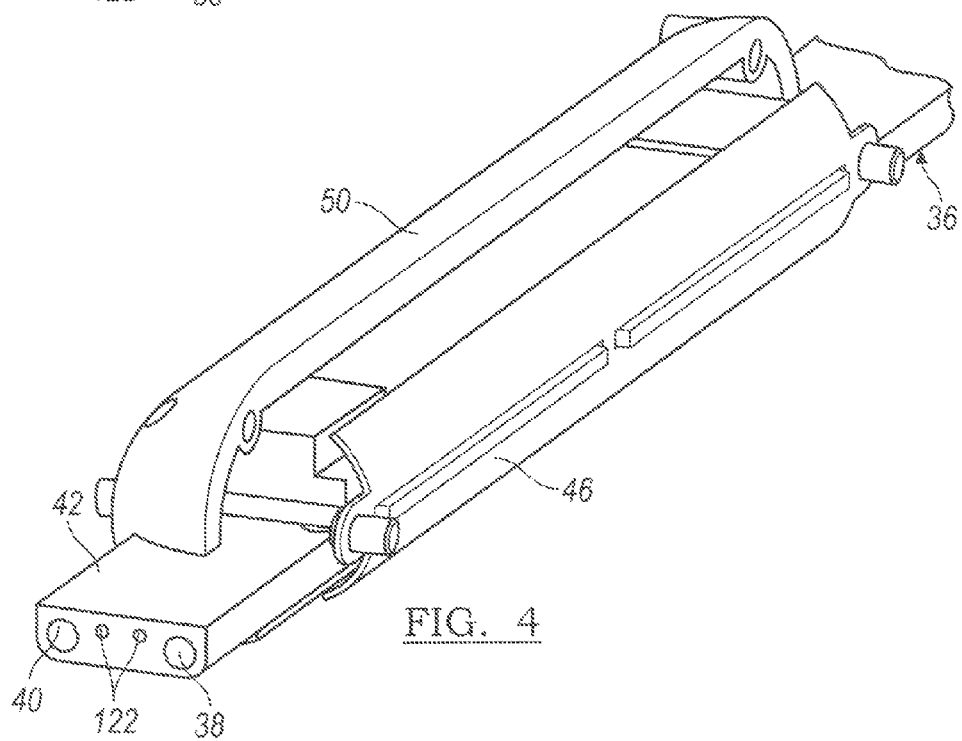
FIG. 4 is a perspective view of the capacitive moisture cable sensor node of FIG. 3 with one half of the housing removed showing the longitudinal part line thereof.
Figure 5:
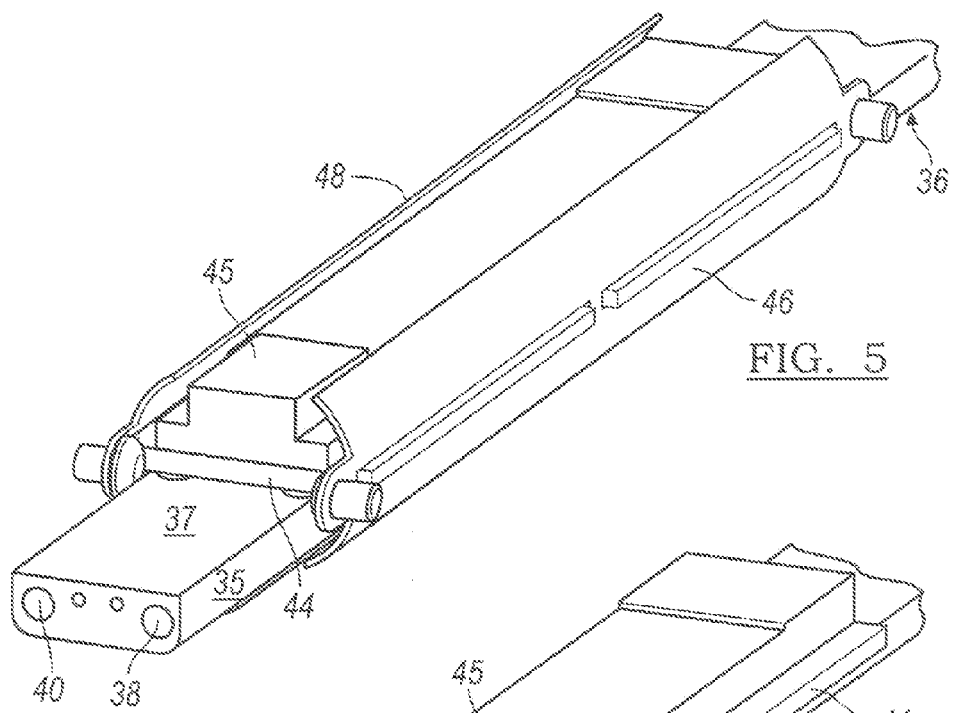
FIG. 5 is a perspective view of the capacitive moisture cable sensor node of FIG. 3 with the housing removed.
Figure 6:
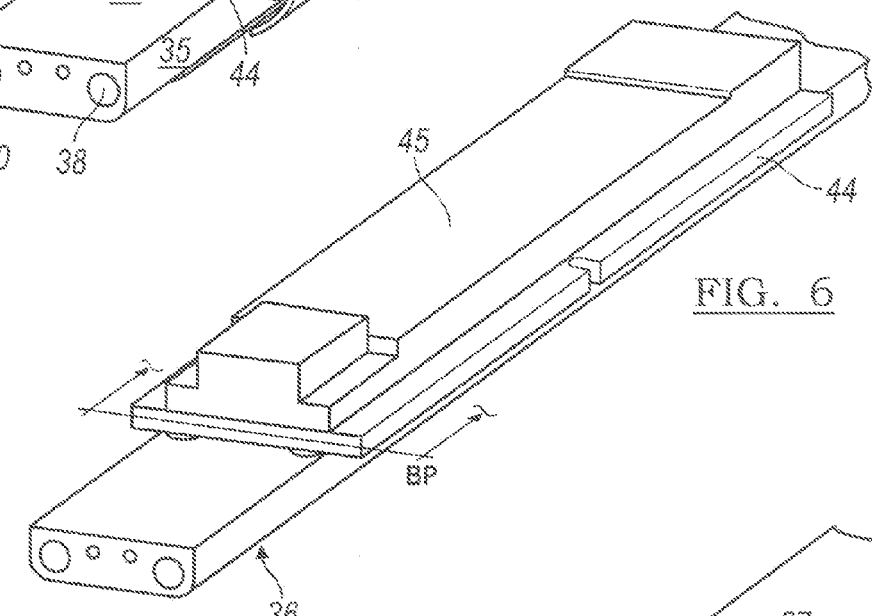
FIG. 6 is a perspective view of the capacitive moisture cable sensor node of FIG. 3 with the housing and capacitive plates removed.
Figure 7:
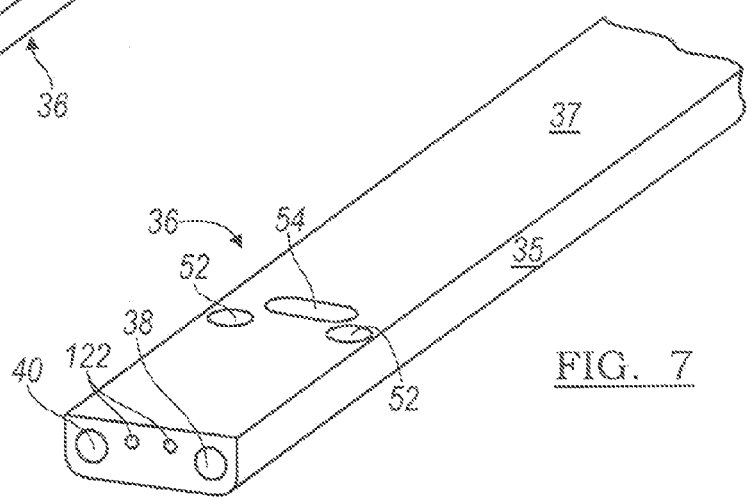
FIG. 7 is a perspective view of the wiring cable of the capacitive moisture cable sensor node of FIG. 3.

Moisture cables 32 are spaced throughout the interior of grain bin 12 as diagramed in FIG. 2. It should be appreciated that FIG. 2 is a diagrammatic representation that has been simplified to improve understanding. Each moisture cable 32 is typically physically suspended from and supported by the roof structure 13 of the grain bin 12. Similarly, data collector 26 associated with grain bin 12 can be provided above the grain storage area, so essentially no downward force is exerted on data collector 26 by grain in grain bin 12. For example, data collector 26 can be mounted to the roof structure outside grain bin 12 or inside grain bin 12 near a top of the roof structure.

Referring to FIGS. 3-7, moisture cables 32 are illustrated in additional detail. Each moisture cable 32 includes a wiring cable 36. Wiring cable 36 includes a pair of main conductors 38 and 40. For example, main conductor 38 can provide the ground with main conductor 40 providing the opposite polarity. Main conductors 38, 40 are spaced apart from each other along a conductor plane CP passing through the conductors. Positioned in the space provided between main conductors 38, 40 are a pair of communication signal wires 122. Conductors 38, 40 and signal wires 122 are insulated from each other and the outside environment by electrically insulating material 42. The overall cross-sectional shape of wiring cable 36 is generally rectangular to allow for increased distance or spacing between main conductors 38, 40, by placing each main conductor adjacent 38, 40 one of the short sides 35 of the rectangular cross-section.

Sensor nodes 34 also include a circuit board 44 positioned against one of the long sides 37 of a rectangular cross-section of wiring cable 36. Circuit board 44 is generally planar with a rectangular shape having primary length and width dimensions in a circuit board plane BP that is parallel to conductor plane CP. Extending along opposing sides defining the length L of the circuit board 44 is a pair of opposing capacitive plates 46, 48. Opposing capacitive plates 46, 48 likewise extend along a corresponding length of the wiring cable 36; adjacent each of the short sides 35 of wiring cable's 36 rectangular cross-section. Circuit board 44 includes circuit board componentry 45 mounted thereon, such as sensor node microprocessor and memory.

Ground plane plate 46 is positioned adjacent a corresponding length of main ground conductor 38, and the opposite polarity plate 48 is positioned adjacent a corresponding length of opposite polarity main conductor 40. Opposing capacitive plates 46, 48 can be positioned generally perpendicular to the conductor plane CP and circuit board plane BP. Each capacitive plate 46, 48 can extend only outside a plane extending along the inside edge of adjacent main conductor 38 or 40 and perpendicular to the conductor plane CP and circuit board plane BP.

Power is provided to circuit board 44 via main conductors 38, 40. Communication to and from each sensor node is provided via signal wires 122. Portion of electrically insulating material 42 is removed to enable signal wires 122 and main conductors 38, 40 to be electrically coupled to circuit board 44 via spring loaded pogo pins. Electrically insulating material 42 can be removed using heat, mechanical abrasion, or another technique to provide a pair of main hollows 52 exposing main conductors 38, 40 and at least one secondary hollow 54 exposing secondary conductors 122.

Circuit board 44, capacitive plates 46, 48, and a corresponding portion of wiring cable 36 are all enclosed within a two part housing 50, that provides a sealed inner space and define each sensor node 34. The inner space can be filled with a foam or gel to protect circuit board 44 and related sensor componentry from vibrations, impact, and environmental contaminates such as moisture. The halves of housing 50 can be coupled together using threaded fasteners. Details of circuit board 44 will now be discussed.

Figure 8:
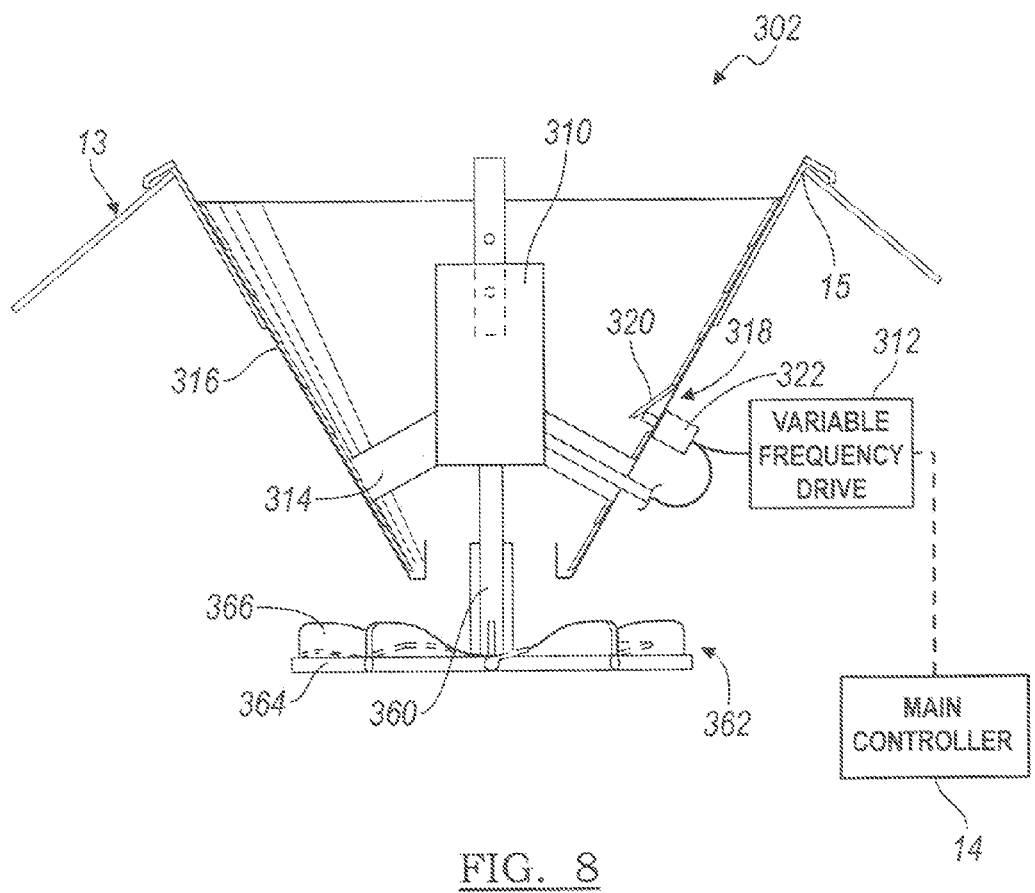
FIG. 8 is a cross-sectional view of a variable speed grain spreader of the system of FIG. 1.

Referring to FIG. 8, grain spreader 302, which is in communication with main controller 14, is illustrated in additional detail. Variable speed grain spreader 302 is coupled to a grain bin roof structure 13 to receive grain flowing into grain bin 12. Grain spreader 302 includes a variable speed motor 310 coupled to a variable frequency drive 312, which is under the control of main controller 14 via the communication link provided by wireless node 24. Variable speed motor 310 is centrally supported by brackets 314 within a funnel member 316 that receives incoming grain flowing through an opening 15 in roof 13 of grain bin 12.

Grain spreader 302 also includes a sensor (or switch) 318 to detect the presence of incoming grain passing through funnel member 316. Sensor 318 is provided on the inside surface of funnel member 316. Sensor 318 includes a hinged plate 320 that bears against a push-button 322. The weight of incoming grain presses against hinge plate 320 which moves push-button 322 into the "on" position. When in the "on" position, grain spreader 302 is activated and operates under the control of main controller 14. Specifically, main controller 14 controls the speed of variable speed motor 310.

Figure 10:
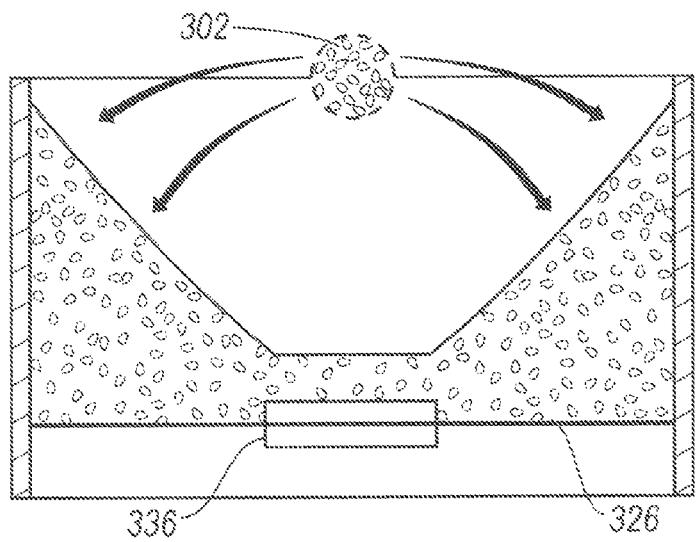
FIGS. 10 and 11 are simplified cross-sectional views of a grain bin, each showing an exemplary inverted cone-shaped grain surface.
Figure 11:
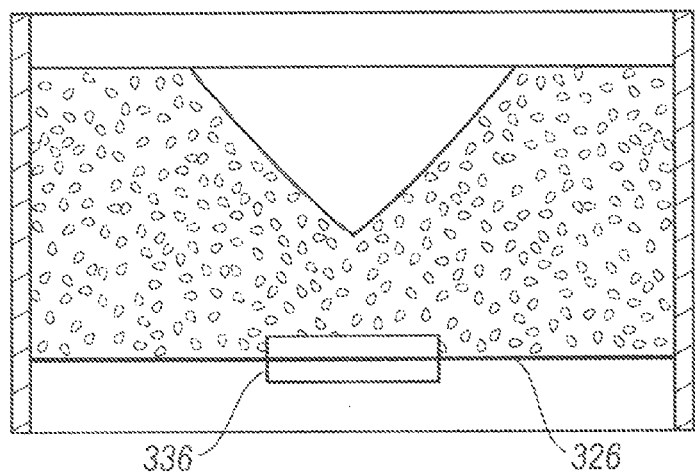

As discussed in detail below, grain spreader 302 can be operated at a relatively high speed in order to provide the grain with an inverted conically-shaped surface. Examples of inverted conically shaped grain surfaces are shown in cross-section in FIGS. 10 and 11. Alternatively, grain spreader 302 can be operated at a relatively low speed in order to provide the grain with a conically-shaped surface. Even at such relatively low speeds, grain fines can be distributed away from the center; e.g., more uniformly throughout the diameter of grain bin 12. An example of a conically shaped grain surface is shown in cross-section in FIG. 12. Variable speed grain spreader 302 can also be operated at a variety of speeds throughout a grain filling operation in order to provide a relatively flat grain surface.

Coupled to the drive shaft 360 of variable speed motor 310 is a rotatable spreader blade 362, which may be of any appropriate configuration. As illustrated, spreader blade 362 includes an octagonal plate 364. A plurality of vanes 366 are pivotably coupled to the upper surface of octagonal plate 364 adjacent the center so each vane can be angularly adjusted along slots in the octagonal plate 364. Such pivotable angular adjustment can be useful for accommodating different sized grain bins.

Returning to FIGS. 1 and 2, main controller 14 can also be in communication with a grain aeration system 305. Grain aeration system 305 includes one or more aeration fans 304. Grain aeration fan 304 typically supplies air to a plenum 324 below a raised grain floor 326 of grain bin 12. Raised grain floor 326 includes apertures 328 through which air from fan 304 passes into the grain storage area 330 of grain bin 12. After passing through the grain, the air typically passes out of the grain bin 12 at or near roof 13 of grain bin 12.

Each aeration fan 304 can be driven by a variable speed motor 332 that are coupled to a variable frequency drive 334, which is under the control of main controller 14 via the communication link provided by wireless node 24. Thus, main controller 14 can control the airflow rate through the grain to manage grain drying efficiency. Potentially applicable methods of controlling the operation of variable speed ventilation fans 304 are described in commonly owned U.S. patent Ser. No. 13/180,797 filed by Bloemendaal et al. on Jul. 12, 2011 and entitled "Bin Aeration System," which is hereby incorporated by reference herein in its entirety.

Grain aeration system 305 can additionally include at least one heater 306 under the control of main controller 14. In the illustrated embodiment, a heater 306 is paired with each aeration fan 304. The heater 306 is provided on the intake side of its paired aeration fan 304. Increasing the temperature, increases the moisture removal capacity of the air as it passes through the grain. Thus, each fan 304 can selectively supply ambient air, or heated air. When heated air is used, the increased efficiency in moisture removal can be balanced against the reduced energy efficiency resulting from powering the heater 306. Thus, in some cases, the heater 306 is controlled to heat the between about 2.5 degrees and 10 degrees Fahrenheit above the ambient temperature.

Main controller 14 can also be in communication with a grain removal auger 308 via the communication link provided by wireless node 24. Grain bins 12 typically include a sump 336 located in the center of grain floor 326 through which grain can be removed from grain bin 12. Grain removal auger 308 operates to transport grain from sump 336 to the exterior of the grain bin 12. Thus, grain removal auger 308 can be under control of main controller 14. The term "auger" as used herein includes any grain removal system known in the art, including screw augers, grain pumps, and devices using paddles. One exemplary grain pump is marketed under the name Hutchinson Grain Pump™ manufactured by Global Industries, Inc. of Grand Island, Nebr.

As discussed below, grain removal auger 308 can be controlled by main controller 14 to remove grain via a centrally located sump 336 in order to provide the grain with an inverted cone-shaped surface. Examples of inverted cone-shaped surfaces are shown in cross-section in FIGS. 10 and 11. An inverted cone shaped grain surface results in a shortened airflow path passing through the grain in the central portion of grain bin 12. In other words, air passing through the grain in an outer radial portion of grain bin 12 has a longer airflow path through the grain.

Figure 12:
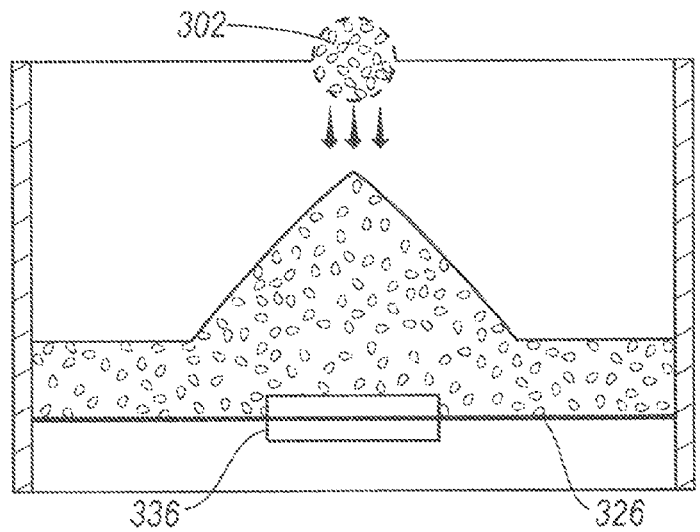
FIG. 12 is a simplified cross-sectional view of a grain bin showing an exemplary cone-shaped grain surface.

Alternatively, grain removal auger 308 can be controlled by main controller 14 to remove grain via one or more radially located sumps (not shown) in order to provide the grain with a conically-shaped surface, similar to what is shown in FIG. 12. A cone shaped grain surface results in a shortened airflow path passing through the grain in the outer radial portion of grain bin 12. In other words, air passing through the grain in a central portion of grain bin 12 has a longer airflow path through the grain.

Figure 9:
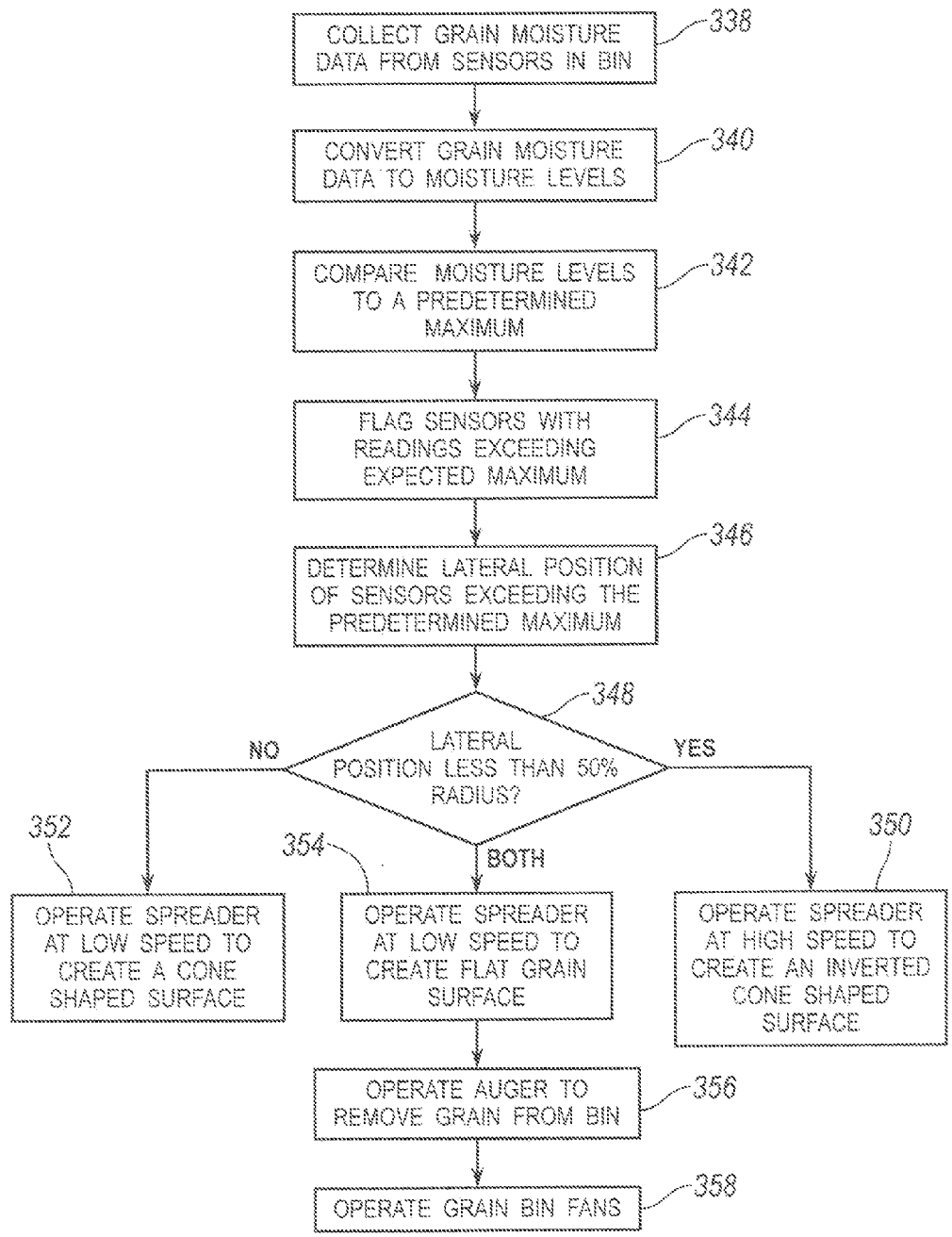
FIG. 9 is a flowchart of certain aspects of the grain bin drying system of FIG. 1.

Referring to FIG. 9, a flowchart is provided for operating the grain bin drying system 10. Raw moisture data is collected from each of a plurality of capacitive moisture sensor nodes 34 provided at predetermined intervals along one or more moisture cables 32 at box 338. The raw moisture data can include reference capacitance data, measured moisture capacitance data, and temperature data. At box 340, the collected raw moisture data from each sensor node 34 can be converted to moisture levels by main controller 14. The moisture content levels as determined by main controller is indicative of the grain moisture content adjacent each sensor node 34. The collection of raw moisture data 338 and conversion into moisture data 340 can be accomplished as described in commonly owned U.S. patent application Ser. No. 13/569,814 entitled "Grain Bin Capacitive Moisture Sensor System" and Ser. No. 13/569,804 entitled "Grain Bin Capacitive Moisture Sensor System and Method" that were both filed on Aug. 8, 2012 by Bloemendaal et al., and which are both hereby incorporated herein by reference in their entirety.

At box 342, the adjacent grain moisture content level determined for each sensor node 34 is compared to a predetermined maximum moisture content level. Any sensor node 34 having a moisture content level that is above the predetermined maximum level is flagged at box 344. The lateral position of each flagged sensor node 34 is determined at box 346. Main controller 14 includes information relating each sensor node address identification to a physical position of the sensor node 34 within grain bin 12. An exemplary data structure map of a portion of memory 18 of main controller 14 is provided in FIG. 13. This locational correlation information can be entered into main controller 14 upon initial installation and set-up of the moisture cables 32 within grain bin 12.

A measured grain moisture content level that is above a predetermined maximum level suggests there is a problematic area (or pocket) of grain adjacent that sensor. Grain spoilage could occur in any such problematic pocket if the grain moisture content level is not brought down. The physical location of each sensor node within the grain bin is important. Thus, main controller 14 can use information regarding the physical location of any flagged sensor nodes 32, in order to take corrective action directed at a problematic pocket of grain.

If the flagged sensor nodes 34 have a lateral position that is less than 50% of the radius of the grain bin at 348, then main controller 14 operates grain spreader 302 at a high speed to create an inverted cone shaped grain surface within grain bin 12 when grain is subsequently added to the grain bin at box 350. If the flagged sensor nodes 34 have a lateral position that is greater than 50% of the radius of the grain bin at 348, then main controller 14 operates grain spreader 302 at a low speed to create a cone shaped grain surface within grain bin 12 when grain is subsequently added to the grain bin at box 352. If the flagged sensor nodes are both greater than and less than 50% of the bin radius, then main controller 14 can operate grain spreader 302 at various speeds to create a generally flat grain surface at box 354. Thus, this process can be performed immediately prior to adding grain to a particular grain bin 12, or in order to determine into which among several grain bins 12 new grain is best added in order to manage any problematic grain pockets.

Additionally or alternatively, main controller 14 can operate grain removal auger 308 to remove grain from grain bin 12 at box 356. For example, when the flagged sensor nodes 34 have a lateral position that is less than 50% of the radius of the grain bin at 348, then main controller 14 can operate grain removal auger to remove grain via centrally located sump 336, thereby creating an inverted cone shaped grain surface within grain bin 12. Removed grain can be returned to the grain bin through opening 15 in the bin roof structure 13, where grain spreader 302 operating at high speed can aid the formation of the inverted cone shaped grain surface within grain bin 12.

Similarly, main controller 14 can operate grain removal auger 308 to remove grain from grain bin 12. For example, when the flagged sensor nodes 34 have a lateral position that is greater than 50% of the radius of the grain bin at 348, then main controller 14 can operate grain removal auger to remove grain via radially located sumps, thereby creating a cone shaped grain surface within grain bin 12. An exemplary grain removal auger system using a plurality of grain removal sumps is described in detail in commonly owned U.S. patent application Ser. No. 12/827,448, filed by Niemeyer et al. on Jun. 30, 2010 and entitled "Circular Bin Unload System and Method," which is hereby incorporated herein by reference in its entirety. Removed grain can be returned to the grain bin through opening 15 in the bin roof structure 13, where grain spreader 302 operating at low speed can aid the formation of the cone shaped grain surface within grain bin 12.

At box 358, main controller 14 operates aeration system 305 to pass air through grain in grain bin 12. The aeration airflow preferentially passes through the grain via the shortened airflow path, with less airflow passing through the grain via the longer airflow path. For example, airflow preferentially passes through the central area of grain bin 12 when an inverted cone-shaped grain surface is provided. In contrast, airflow preferentially passes through the radially outer area when a cone-shaped grain surface is provided. In this way, main controller 14 can cause increased aeration airflow to pass through any high-moisture content area in the grain bin to preferentially dry such high moisture content grain. Main controller 14 can also control the overall airflow rate by controlling the speed of fan 304 and the airflow temperature of the aeration air by controlling heater 306.

A brief discussion of an exemplary process main controller 14 can use to convert raw sensor data into a calculated moisture content follows. A curve based on empirical data that plots a ratio of measured capacitance to reference capacitance against actual measured moisture content can be used to create a capacitance look-up table.

Since capacitance varies by temperature, the results from this capacitance look-up table can be adjusted based upon temperature data provided by sensor node 34. A curve based on empirical data that plots a percent change in moisture content against measured temperatures can be used to create a look-up table to determine a temperature adjustment factor. Thus, the moisture content level result obtained using the capacitance look-up table can be multiplied by a temperature adjustment factor obtained from the temperature look-up table to account for the temperature at the time of the capacitance measurement.

The measured capacitance can also vary in relation to how compact the grain is surrounding the sensor node. Thus, a curve based on empirical data that plots a percent change in moisture content against the depth of the sensor node below the surface of the grain in grain bin 12. This data plot can be used to create a look-up table to determine a compaction adjustment factor. The moisture content level result obtained using the capacitance look-up table can be multiplied by a compaction adjustment factor obtained from the compaction look-up table to account for the depth of the sensor node 34 below the grain surface.

The depth of sensor nodes 34 below the surface of the grain can be determined by main controller 14. For example, if there is no grain surrounding a particular sensor node 34, then system 10 will record a no-adjacent-grain value such as zero for any data that is outside a predetermined range for moisture capacitance. For example, a ratio of measured capacitance to reference capacitance that is less than 3% for a sensor node 34 can indicate that there is no grain adjacent that sensor node 34. Thus, if this ratio is outside a predetermined range, such as being less than a predetermined value, it can be concluded that there is no grain adjacent the sensor. As a result, main controller 14 can approximate the surface of the grain in grain bin 12 based upon such anomalous readings. For example, with sensor nodes 34 spaced four feet apart, system 10 can assume the grain bin fill height at a moisture cable 32 is two feet below the lowest sensor node returning a no-adjacent-grain-value.

In addition, to enabling main controller 14 to calculate a sensor node 34 depth for use in applying a grain compaction factor, this estimated grain surface information can be used to confirm whether the grain surface has a cone-shape, or a conical-shape. For example, main controller 14 can compare the estimated grain surface height for moisture cables 32 positioned radially (or laterally) closer to the center of grain bin 12 to the estimated grain surface height for moisture cables 32 positioned radially (or laterally) farther away from the center of grain bin 12. This can confirm whether the grain surface has a desired shape. For example, when progressively inner (i.e., closer to the center) moisture cables 32 have a grain surface height that is meaningfully greater than the grain surface height of progressively outer (i.e., farther from the center) moisture cables, then the grain has a cone-shaped surface. Such a grain surface provides a shortened (or lower resistance) air flow path through problematic grain pocket(s) in an outer radial area of the grain bin relative to grain flow paths through grain in the central area of grain bin 12.

In contrast, when progressively inner (i.e., closer to the center) moisture cables 32 have a grain surface height that is meaningfully less than the grain surface height of progressively outer (i.e., farther from the center) moisture cables, then the grain has an inverted cone-shaped surface. Such a grain surface provides a shortened (or lower resistance) air flow path through problematic grain pocket(s) in the central area of grain bin 12 relative to grain flow paths through grain in an outer radial area of grain bin 12. In both cases, a low resistance airflow path through the problematic area or pocket of grain can be created, and ventilation fans and heaters can be used to cause air to flow preferentially through and treat the problematic area or pocket of grain.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system for drying grain in a grain bin comprising;
a plurality of moisture sensors positioned within the grain bin at various spaced-apart locations throughout the grain bin;
the plurality of moisture sensors being coupled to a controller configured to determine a grain moisture level adjacent each moisture sensor;
the controller being configured to compare each grain moisture level to a predetermined maximum moisture level;
the controller being coupled to one of: a grain spreader configured to selectively distribute grain coming into the grain bin; a grain discharge auger configured to selectively remove grain from the grain bin; or both;
the controller being configured to operate the one of: the grain spreader, the grain discharge auger, or both, to create a shortened airflow path encompassing the moisture sensors having determined grain moisture levels above the predetermined maximum moisture level;
the controller being coupled to a fan associated with the grain bin and configured to provide airflow through grain in the grain bin;
the controller being configured to operate the fan, wherein greater airflow is provided through the grain along the shortened airflow path than is provided along airflow paths through the grain outside the shortened airflow path.

2. The system for drying grain in a grain bin of claim 1, wherein the one of: a grain spreader configured to selectively distribute grain coming into the grain bin; a grain discharge auger configured to selectively remove grain from the grain bin; or both, is a grain spreader comprising a variable speed motor coupled to the controller to selectively distribute grain coming into the grain bin.

3. The system for drying grain in a grain bin of claim 2, wherein the controller is further coupled to an auger configured to remove grain from the grain bin via a central sump.

4. The system for drying grain in a grain bin of claim 1, wherein the moisture sensors are capacitive moisture sensors provided at intervals along at least one capacitive moisture sensor cable.

5. The system for drying grain in a grain bin of claim 1, wherein the plurality of moisture sensors are coupled to the controller via a wireless interface.

6. The system for drying grain in a grain bin of claim 1, further comprising a heater configured to heat the airflow provided by the fan before the airflow passes through grain in the grain bin, and wherein the controller is coupled to the heater and the controller is configured to operate the heater.

7. The system for drying grain in a grain bin of claim 1, wherein the controller is configured to determine when there is no grain adjacent moisture sensors based on sensor data that is outside a predetermined range; wherein the controller can estimate a shape and position of a grain surface in the grain bin.

8. A system for drying grain in a grain bin comprising;
a plurality of capacitive moisture sensors positioned within the grain bin at various spaced-apart locations throughout the grain bin;
the plurality of capacitive moisture sensors being coupled to a controller configured to determine a grain moisture level adjacent each moisture sensor;
the controller being configured to compare each grain moisture level to a predetermined maximum moisture level;
the controller being coupled to a variable speed grain spreader configured to selectively distribute grain coming into the grain bin;
the controller being configured to operate the grain spreader to create one of an inverted cone-shaped grain surface, and a cone-shaped surface, wherein a shortened airflow path encompasses the moisture sensors having determined grain moisture levels above the predetermined maximum moisture level;
the controller being coupled to a fan associated with the grain bin and configured to provide airflow through grain in the grain bin;
the controller being configured to operate the fan, wherein greater airflow is provided through the grain along the shortened airflow path than is provided along airflow paths through the grain outside the shortened airflow path.

9. The system for drying grain in a grain bin of claim 8, wherein the plurality of moisture sensors are coupled to the controller via a wireless interface.

10. The system for drying grain in a grain bin of claim 8, further comprising a heater configured to heat the airflow provided by the fan before the airflow passes through grain in the grain bin, and wherein the controller is coupled to the heater and the controller is configured to operate the heater.

11. The system for drying grain in a grain bin of claim 8, wherein the controller is configured to determine when there is no grain adjacent moisture sensors based on sensor data that is outside a predetermined range; and wherein the controller is configured to estimate a grain surface in the grain bin.

12. The system for drying grain in a grain bin of claim 8, wherein the controller is configured to operate the grain spreader at a high speed to create an inverted cone-shaped grain surface.

13. A method of drying grain in a grain bin comprising;
coupling a controller to a plurality of moisture sensors positioned within the grain bin at various spaced-apart locations throughout the grain in the grain bin;
the controller determining a grain moisture level adjacent each moisture sensor;
the controller comparing the grain moisture level to a predetermined maximum moisture level;
coupling the controller to a grain spreader configured to selectively distribute incoming grain into the grain bin;
the controller operating the grain spreader to distribute incoming grain to create a shortened airflow path through the grain in the grain bin that encompasses the moisture sensors having determined grain moisture levels above the predetermined maximum moisture level;
coupling the controller to a fan coupled to the grain bin and configured to provide airflow through the grain in the grain bin;
the controller operating the fan, wherein greater airflow is provided through the grain along the shortened airflow path than is provided along airflow paths through the grain outside the shortened airflow path.

14. The method of drying grain in a grain bin of claim 13, further comprising providing the grain spreader with a variable speed motor coupled to and operated by the controller.

15. The method of drying grain in a grain bin of claim 13, further comprising providing an auger configured to remove grain from the grain bin via a central sump; coupling the controller to the auger; the controller operating the auger to remove grain from the grain bin through the central auger.

16. The method of drying grain in a grain bin of claim 15, further comprising reintroducing the removed grain into the grain bin and selectively distributing the removed grain via the grain spreader.

17. The method of drying grain in a grain bin of claim 13, further comprising providing the moisture sensors as capacitive moisture sensors positioned at intervals along at least one capacitive moisture sensor cable.

18. The method of drying grain in a grain bin of claim 13, wherein coupling the controller to the plurality of moisture sensors comprises providing a wireless interface.

19. The method of drying grain in a grain bin of claim 13, further comprising providing a heater configured to heat the airflow provided by the fan before the airflow passes through grain in the grain bin, and coupling the controller to the heater, and the controller operating the heater.

20. The method of drying grain in a grain bin of claim 13, further comprising the controller determining when there is no grain adjacent the moisture sensors based on sensor data that is outside a predetermined range and estimating a shape and position of a grain surface in the grain bin.

* * * * *